United States Patent [19]

Nowakowski et al.

[11] Patent Number: 4,772,712
[45] Date of Patent: Sep. 20, 1988

[54] PHENOXYPHENYL-SUBSTITUTED TETRAZOLINONES

[75] Inventors: Mark A. Nowakowski, Haddam; James A. McGuiness, Naugatuck; Allyn R. Bell; Allen R. Blem, both of Cheshire, all of Conn.

[73] Assignee: Uniroyal Chemical Company, Inc., Middlebury, Conn.

[21] Appl. No.: 142,608

[22] Filed: Jan. 11, 1988

[51] Int. Cl.$^4$ ............... C07D 401/04; C07D 409/04; C07D 257/04
[52] U.S. Cl. ..................................... 546/276; 548/251
[58] Field of Search ......................... 548/251; 546/276

[56] References Cited

U.S. PATENT DOCUMENTS 3,928,416 12/1975 Bayer et al. ..................... 260/471
4,209,318  6/1980 Johnson ................................. 71/88
4,618,365 10/1986 Covey et al. ........................... 71/92

FOREIGN PATENT DOCUMENTS 8401799 5/1984 PCT Int'l Appl. .

OTHER PUBLICATIONS

Chem.Abs. 94:46981q (Durr et al.).
Chem.Abs. 94:156539j (Swithenbank et al.).
Chem.Abs. 95:150174k (Barton).
Horwitz et al., JACS, 81 3076 (1959).
Tsuge et al., J. Org. Chem., 45 5130 (1980).

Primary Examiner—Richard L. Raymond
Assistant Examiner—D. B. Springer
Attorney, Agent, or Firm—William E. Dickheiser

[57] ABSTRACT

Tetrazolinone derivatives having substituted thereon an (optionally substituted) phenoxyphenyl moiety exhibit unexpectedly desirable pre- and post-emergent herbicidal as well as plant growth regulant activity. In addition, herbicidal and plant growth regulatory compositions comprising such novel compounds as well as methods of controlling the growth of weeds and regulating the growth of plants employing such novel compounds are shown. Moreover, a process for producing such compounds is also described.

2 Claims, No Drawings

PHENOXYPHENYL-SUBSTITUTED TETRAZOLINONES

FIELD OF THE INVENTION

This invention relates to a novel class of tetrazolinone derivatives having substituted thereon an (optionally substituted) phenoxyphenyl moiety, which compounds exhibit unexpectedly desirable pre- and post-emergent herbicidal activity as well as plant growth regulatory activity. In other aspects, this invention relates to a herbicidal composition comprising such novel compounds as well as to a method of controlling the growth of weeds employing the novel compounds of this invention. Moreover, in other aspects this invention relates to a plant growth regulant composition comprising such compounds as well as to a method of controlling the growth of plants employing the novel compounds of this invention. In yet another aspect, this invention relates to a process of producing such compounds.

BACKGROUND OF THE INVENTION

The need for effective herbicides, both preemergence and postemergence, needs no special emphasis. The control of weeds and undesirable vegetation is of great economic importance since weed competition inhibits the production of foliage, fruits and/or seeds and may reduce the quality of the harvested crop. Weed control is essential for maximum production of many agronomic and horticultural crops including soybeans (*Glycine max* (L.) Merr.), peanuts (*Archis hypogaea* L.) and rice (*Oryza sativa* L.). Furthermore, weeds on non-cropped areas may cause a fire hazard, undesirable drifting of sand or snow, or irritation to persons with allergies. Thus, suppression of undesirable weed growth is very advantageous.

Moreover, the need for agricultural chemicals having significant effects on the growth and development of crop plant species is similarly well known. The compounds of this invention are useful as plant growth regulators when employed in amounts effective to regulate the growth of plants, in admixture with a carrier therefor. It will be understood that the term plant as used herein includes plant parts such as foliage, roots, flowers, stems and seeds. Depending on crop, variety, dosage, time of application and certain cultural practices, growth regulating effects which may be obtained include one or more of the following: dwarfing, cessation of terminal growth, inhibition of axillary and intercalary growth, retardation of internode elongation, inhibition of flowering or reproductive development, and the like.

One form of such plant growth regulation which is particularly economically important is the field of harvest aid compounds. The field of harvest aid utilization includes a wide variety of primary effects, including the defoliation of the crop plant; the desiccation of its leaves, stems, and other aerial organs; the control of late-season regrowth (e.g., for cotton); the promotion or inhibition of fruit or flower abscission; the concentration of crop maturity; and the enhancement of consumer-preferred quality factors.

Under normal conditions, many crop plants do not mature uniformly or in a timely fashion that would facilitate an efficient and optimum harvest, either due to equipment scheduling or weather considerations. Crops such as cottom, potato, sunflower, and seed legumes require either desiccation or defoliation before harvest can be effectively accomplished. Thus, for example, when cotton is not defoliated the leaves can interfere with mechanized picking apparati which are frequently employed. Also, leaves can contaminate the cotton lint with trash or green stain, which reduces the quality of the fiber or reduces the efficiency of the ginning process. Likewise, potato vines need to be desiccated for efficient mechanical digging. In addition, upon desiccation of potato leaves and stems, the tuber skin matures and becomes less susceptible to damage from the digger and postharvest handling. Seed legumes and sunflowers are also mechanically harvested, and this process is facilitated if the leaves and stems are removed or desiccated. As with cotton and potato, such defoliation or desiccation also ripens the seed uniformly, accelerates the rate of seed maturation, and conditions the pod or head for easy harvest.

While a large number of compounds possessing herbicidal and/or plant growth regulatory activity are known, it would be nonetheless desirable to possess additional compounds which would effectively control the growth of unwanted vegetation and/or regulate the growth of commercially desirable plants.

U.S. Pat. No. 4,618,365 to Covey et al discloses certain carbamyl-substituted tetrazolinones useful as herbicides. Somewhat similarly, PCT International Application No. PCT/U.S.84/01799 (Theodoridis et al) shows certain phenyl substituted tetrazolinone derivatives which exhibit herbicidal activity.

U.S. Pat. Nos. 3,928,416 to Bayer et al and 4,209,318 to Johnson both show herbicidal 4-trifluoromethyl-nitrodiphenyl ethers. Similar herbicidal diphenyl ethers are disclosed in Chemical Abstracts 94:46981q (1981) (Durr et al); Chemical Abstracts 94; 156539j (1981) (Swithenbank et al); and Chemical Abstracts 95; 150174k (1981) (Barton).

However, neither of these publications suggest that phenoxyphenyl-substituted tetrazolinone derivatives would exhibit herbicidal activity and/or plant growth regulatory activity to a desirable degree.

Accordingly, it is an object of this invention to provide a new class of compounds which exhibit an unexpectedly desirable degree of herbicidal and/or plant growth regulatory activity.

It is another object of this invention to provide novel herbicidal compositions comprising such phenoxyphenyl-substituted tetrazolinones.

It is yet another object of this invention to provide a method for controlling weeds employing such herbicidal compositions.

It is a further object of this invention to provide plant growth regulatory compositions comprising such novel compounds.

It is an additional object of this invention to provide a method for regulating the growth of plants employing such plant growth regulatory compositions.

The above objects and other additional objects will become more fully apparent from the following description and accompanying Examples.

SUMMARY OF THE INVENTION

In one aspect, this invention relates to a compound of the formula:

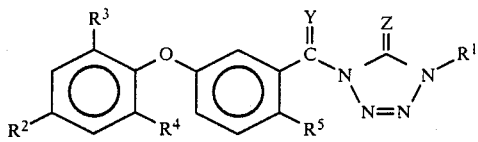 (I)

wherein:
Y is oxygen or sulfur;
Z is oxygen or sulfur;
$R^1$ is
  $C_1-C_{18}$ alkyl,
  $C_1-C_{12}$ haloalkyl,
  $C_2-C_{12}$ alkoxyalkyl,
  $C_2-C_{12}$ alkylthioalkyl,
  $C_3-C_{10}$ alkenyl,
  $C_3-C_{10}$ cycloalkyl,
  $C_5-C_{10}$ cycloalkenyl,
  $C_7-C_{10}$ bridged cycloalkyl or cycloalkenyl,
  $C_7-C_9$ arylalkyl,
  $C_3-C_{12}$ alkoxycarbonylalkyl,
  $C_5-C_6$ aryl,
  naphthyl,
  pyridyl,
  thienyl, or
  phenyl substituted with 1-3 substituents each independently selected from the group consisting of halogen, cyano, nitro, $C_1-C_4$ haloalkyl, $C_1-C_4$ alkyl, $C_2-C_4$ dialkylamino, $C_1-C_4$ alkoxy, $C_1-C_4$ alkylthio, haloalkoxy, phenoxy and phenoxy substituted with one or more members selected from the group consisting of halogen, cyano, nitro, $C_1-C_3$ haloalkyl and $C_1-C_3$ haloalkoxy;
$R^2$ and $R^3$ are each independently halogen, cyano, nitro, $C_1-C_4$ alkyl, $C_1-C_4$ haloalkyl, $C_1-C_4$ alkoxy or $C_1-C_4$ haloalkoxy;
$R^4$ is hydrogen, halogen or trihalomethyl; and
$R^5$ is hydrogen, halogen, cyano, nitro, carboxyl, $C_2-C_8$ alkoxycarbonyl or of the formula:

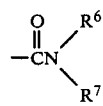

wherein $R^6$ and $R^7$ are each independently hydrogen or $C_1-C_4$ alkyl.

In another aspect, this invention relates to a herbicidal composition comprising:
(A) a compound having the structure of formula (I) above; and
(B) a suitable carrier.

In yet another aspect, this invention relates to a method of controlling weeds, which method comprises applying a herbicidally effective amount of a composition comprised of:
(A) a compound having a structure in accordance with formula (I), and
(B) a suitable carrier.

In another aspect, this invention relates to a plant growth regulant composition comprising:
(A) a compound having the structure of formula (I) above; and
(B) a suitable carrier.

In yet another aspect, this invention relates to a method of regulating the growth of plants, which method comprises applying a plant growth regulatory effective amount of a composition comprised of:
(A) a compound having the structure of formula (I) above; and
(B) a suitable carrier.

In a further aspect, this invention relates to a process for preparing a compound of the structure:

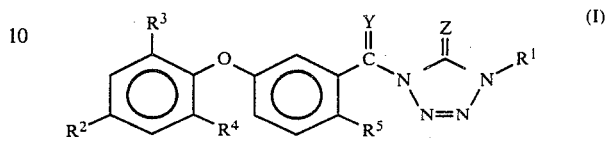 (I)

wherein $R^1$, $R^2$, $R^3$, $R^4$, $R^5$, Y and Z are as defined for formula (I) above, which process comprises reacting a compound of the formula:

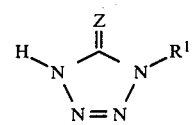

wherein $R^1$ and Z are as defined above; with a compound of the formula:

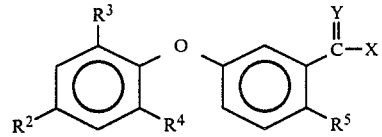

wherein X is halogen and Y, $R^2$, $R^3$, $R^4$, and $R^5$ are as defined above,
in the presence of an acid acceptor.

DETAILED DESCRIPTION OF THE INVENTION

This invention is directed to a compound having the formula:

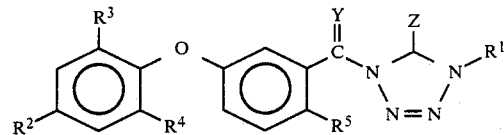

wherein:
Y is oxygen or sulfur;
Z is oxygen or sulfur;
$R^1$ is
  $C_1-C_{18}$ alkyl,
  $C_1-C_{12}$ haloalkyl,
  $C_2-C_{12}$ alkoxyalkyl,
  $C_2-C_{12}$ alkylthioalkyl,
  $C_3-C_{10}$ alkenyl,
  $C_3-C_{10}$ cycloalkyl,
  $C_5-C_{10}$ cycloalkenyl,
  $C_7-C_{10}$ bridged cycloalkyl or cycloalkenyl,
  $C_7-C_9$ arylalkyl,
  $C_3-C_{12}$ alkoxycarbonylalkyl,
  $C_5-C_6$ aryl,
  naphthyl,
  pyridyl,
  thienyl, or phenyl substituted with 1-3 substituents each independently selected from the group consisting of halogen, cyano, nitro, $C_1$-$C_4$ haloalkyl, $C_1$-$C_4$ alkyl, $C_2$-$C_4$ dialkylamino, $C_1$-$C_4$ alkoxy, $C_1$-$C_4$ alkylthio, haloalkoxy, phenoxy and phenoxy substituted with one or more members selected from the group consisting of halogen, cyano, nitro, $C_1$-$C_3$ haloalkyl and $C_1$-$C_3$ haloalkoxy;

$R^2$ and $R^3$ are each independently halogen, cyano, nitro, $C_1$-$C_4$ alkyl, $C_1$-$C_4$ haloalkyl, $C_1$-$C_4$ alkoxy or $C_1$-$C_4$ haloalkoxy;

$R^4$ is hydrogen, halogen or trihalomethyl; and $R^5$ is hydrogen, halogen, cyano, nitro, carboxyl, $C_2$-$C_8$ alkoxycarbonyl or of the formula:

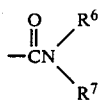

wherein $R^6$ and $R^7$ are each independently hydrogen or $C_1$-$C_4$ alkyl.

Preferably,

Y is oxygen;

Z is oxygen;

$R^2$ is chlorine, fluorine or trifluoromethyl;

$R^3$ is chlorine or trifluoromethyl;

$R^4$ is hydrogen;

$R^5$ is nitro; and $R^1$ is phenyl or phenyl having 1-3 substitutents, each independently selected from the group consisting of halogen, cyano, nitro, haloalkyl, haloalkoxy and 1-naphthyl.

The compounds of this invention are prepared by reacting a tetrazoline of the formula:

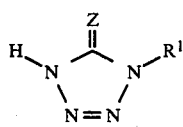

with a phenoxyphenylhalide of the formula:

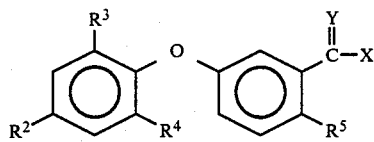

wherein $R^2$, $R^3$, $R^4$, $R^5$, Y and Z are defined in formula (I) above; and wherein X is halogen, preferably chlorine.

The tetrazolinone reactants may be readily prepared by one of ordinary skill in the art following processes such as those described in Horwitz et al. JACS 81 3076 (1959) and Tsuge et al, J. Org. Chem., 45 5130 (1980).

The phenoxyphenyl halide may be prepared by process such as that described in U.S. Pat. No. 3,928,416. Typically, these processes involve the reaction of a (substituted) phenol, or the potassium or sodium salt of the phenol, with a suitably substituted halobenzene, such as a chloro- or fluorobenzene, in the presence of an alkaline agent.

The tetrazolinone and phenoxyphenyl halide reactants are reacted in the presence of a suitable acid acceptor, such as a tertiary amine (e.g., triethylamine), pyridine, potassium carbonate and the like, in order to produce the final compounds. This reaction is typically conducted in a nonreactive organic solvent such as methylene chloride. The reactants are preferably employed in about equimolar ratios, generally of between about 1.25:1 and 1:1.25 moles of tetrazolinone to moles of phenoxyphenyl halide.

The crude reaction product so produced is then typically isolated from the reaction medium by first being washed with water, and then by a dilute acid solution (e.g., 1% HCl). The water insoluble phase is then generally dried (e.g., by treatment with $MgSO_4$) filtered and the solvent distilled off under vacuum. The residue may then be further purified by conventional means, such as by column chromatography or by recrystallization.

If desired, those phenoxyphenyl-substituted tetrazolinones represented by structural formula (I) wherein $R^5$ is carboxyl may be converted to their corresponding agriculturally acceptable salts by reacting the particular phenoxyphenyl-substituted tetrazolinone with the appropriate acid (either anhydrous or aqueous). Such reaction may employ an inert organic solvent or an aqueous solvent, and typically a reaction temperature of between about 0° and about 50° C. is employed. The resultant salt is then isolated and purified by known methods.

The compositions of this invention are comprised of (a) an herbicidally or plant growth regulatory effective amount of a novel phenoxyphenyl-substituted tetrazolinone of this invention and (b) a suitable carrier. Such compositions may comprise one or more of the novel compounds of this invention.

To prepare such agriculturally useful compositions, the phenoxyphenyl-substituted tetrazolinone may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the agriculturally active compound may be impregnated on finely-divided or granular inorganic or organic carriers such as attapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic material (e.g., corn cob). The wettable powder may then be dispersed in water and sprayed on the soil surface, or on crop or weed plants.

Similarly, an emulsifiable concentrate may be prepared by dissolving the chemical in a solvent such as benzene, toluene, or other aliphatic or aromatic hydrocarbon to which a surface active dispersing agent generally has been added. The emulsifiable concentrate may then be dispersed in water and applied by spraying.

The concentration of active chemical in the composition may vary widely typically ranging from about 1 to about 95% by weight. The concentration of active chemical in dispersions applied to the soil, seed or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulations may be applied to the soil either as a liquid or a granule.

For use as a preemergence herbicide the compound of this invention is typically applied at a rate of from about 0.05 to about 25 pounds per acre (about 0.056 to about 28 kg/ha) to soil which contains weed and crop seed. Such application is made either to the surface of the soil or into the upper one to three inches (2.5 to 7.5 cm.) of soil. When employed as a postemergence herbicide or as a plant growth regulator the derivative is typically applied at a rate of from about 0.05 to about 25 pounds per acre (about 0.056 to about 28 kg/ha) to the aerial portions of weeds or crop plants.

The most suitable dosage of application, and the most effective type and amount of adjuvant substance will depend on a number of factors, including the plant species; the stage of plant development; the method of application; the specific biological effect desired; the air and soil temperature and the quantity and intensity of rainfall before and after treatment; the soil type, pH, fertility and moisture and organic matter content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. However, one skilled in the art can, by routine experimentation, readily determine optimum conditions for the employment of any particular phenoxyphenyl-substituted tetrazolinone compound.

EXAMPLES

The following Examples are intended to further illustrate the invention and are not intended to limit the scope of the invention in any manner whatsoever.

EXAMPLE 1

Production of 1-(2-ethoxyphenyl)-4-(1,1'-oxydiphenyl-2'-chloro-4'-trifluoromethyl-4-nitro-3-carboxy)-5(4H)-tetrazolinone (Compound 5)

To a solution of 2-nitro-5 [2-chloro-4-(trifluoromethyl)-phenoxyl] benzoyl chloride II (6.50 grams, 17.5 mmoles) in 20 ml methylene chloride was added 2-ethoxyphenyl-5-(4H)tetrazolinone (3.62 grams, 17.5 mmoles). The resultant slurry was stirred and cooled by a dry-ice acetone bath. A solution of triethylamine (1.77 grams, 17.5 mmoles., 2.44 ml) in 20 ml methylene chloride was then added dropwise over a 5-minute period while stirring the contents of the reaction flask. The cooling bath was then removed and the reaction mixture stirred at room temperature under an inert atmosphere overnight. The reaction mixture was then extracted in succession with water, 1% HCl, saturated sodium bicarbonate solution and saturated sodium chloride solution. The organic phase was dried over MgSO4, filtered and concentrated to dryness. The foam residue was dissolved in 8 ml of ethylacetate and purified by flash-chromatography (stationary phase—100 grams silica gel; mobile phase=20% ethylacetate in hexane). Vacuum concentration of the product containing eluant yielded 6 grams of the desired material.

EXAMPLE 2

Preparation of 1-methyl-4-(1,1'-oxydiphenyl-2'-chloro-4'-trifluoromethyl-4-nitro-3-carboxy)-5(4H)-tetrazolinone (Compound 3)

To a solution of 2-nitro-5[2-chloro-4-(trifluoromethyl)-phenoxyl] benzoyl chloride II (3.80 grams, 10.0 mmoles ) dissolved in 10 ml methylene chloride was added methyl-5-(4H)tetrazolinone and the stirring mixture cooled with a dry ice-acetone bath. Triethylamine (1.01 grams, 10.0 mmoles, 1.39 ml) was then added dropwise over a one minute period after which the mixture was allowed to warm to room temperature and stirred for two hours. Upon dilution of the reaction mixture with 20 ml methylene chloride the solution was extracted successively with water, 1% HCl, and water, the organic phase dried over MgSO4, filtered then concentrated to dryness. The resultant foam residue was dissolved in 4 ml toluene then crystallized upon scratching the flask wall. The precipitate was filtered, washed with toluene, then hexane and air dried to yield 2.02 g, of the desired product.

EXAMPLE 3

Additional compounds within the scope of this invention were prepared using essentially the procedures outlined above. The structures and melting points of these compounds are summarized in Tables I and II below.

TABLE I

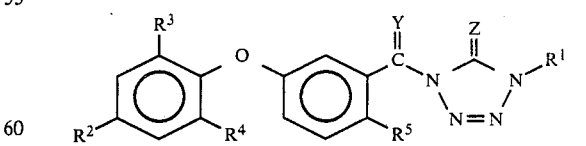

| Cpd. No. | R¹ | R² | R³ | R⁴ | R⁵ | Y | Z | M.P. °C. |
|---|---|---|---|---|---|---|---|---|
| 1 | 1-naphthyl | $CF_3$ | Cl | H | $NO_2$ | O | O | 75–110 |
| 2 | n-$C_8H_{17}$ | $CF_3$ | Cl | H | $NO_2$ | O | O | 90–93 |
| 3 | $CH_3$ | $CF_3$ | Cl | H | $NO_2$ | O | O | 152.5–154 |

TABLE II

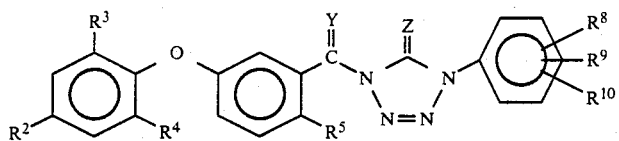

| Cpd. No. | R² | R³ | R⁴ | R⁵ | R⁸ | R⁹ | R¹⁰ | Y | Z | M.P. °C. |
|---|---|---|---|---|---|---|---|---|---|---|
| 4 | CF₃ | Cl | H | NO₂ | H | H | H | O | O | 131-133 |
| 5 | CF₃ | Cl | H | NO₂ | 2-OC₂H₅ | H | H | O | O | 67-75 |
| 6 | CF₃ | Cl | H | NO₂ | 4-OCH₃ | H | H | O | O | 58.5-60.5 |
| 7 | CF₃ | Cl | H | NO₂ | 4-OCH₆H₅ | H | H | O | O | 55-58 |
| 8 | CF₃ | Cl | H | NO₂ | 2-Cl | H | H | O | O | 123-126 |
| 9 | CF₃ | Cl | H | NO₂ | 2-F | H | H | O | O | 99-103 |
| 10 | CF₃ | Cl | H | NO₂ | 3-Cl | H | H | O | O | 121-125 |
| 11 | CF₃ | Cl | H | NO₂ | 3-Br | H | H | O | O | 127.5-130 |
| 12 | CF₃ | Cl | H | NO₂ | 3-F | H | H | O | O | 133-138 |
| 13 | CF₃ | Cl | H | NO₂ | 4-I | H | H | O | O | 140-146 |
| 14 | CF₃ | Cl | H | NO₂ | 4-NO₂ | H | H | O | O | 168-170 |
| 15 | CF₃ | Cl | H | NO₂ | 3-CF₃ | H | H | O | O | 132-137 |
| 16 | CF₃ | Cl | H | NO₂ | 2-OCH₃ | 4-OCH₃ | H | O | O | 113-116 |
| 17 | CF₃ | Cl | H | NO₂ | 2-Cl | 3-Cl | H | O | O | 131-141 |
| 18 | CF₃ | Cl | H | NO₂ | 2-Cl | 6-Cl | H | O | O | 120-123 |
| 19 | CF₃ | Cl | H | NO₂ | 3-CH₃ | 4-CH₃ | H | O | O | 142-143 |
| 20 | CF₃ | Cl | H | NO₂ | 2-Cl | 4-Cl | 5-Cl | O | O | 161-168 |

EXAMPLE 4

Preemergence Control

To illustrate the effectiveness of the novel tetrazolinone derivative compounds of this invention as preemergence herbicides, 300 mg of each of the below listed compounds were dissolved in 10 ml acetone to which 30 mg of an emulsifying agent, ethoxylated sorbitran monolaurate, were added. The solution was diluted to 100 ml with distilled water. Ten milliliters of the 3000 ppm solution were diluted to 250 ppm with distilled water. The chemical was applied at the rate of 10 lb/A (11.2 kg/ha) by drenching 46 ml of the 250 ppm solution on the surface of soil in 4½ inch (11.25 cm.) plastic pots wherein seeds of the following weeds had been planted: velvet leaf (*Abutilon theophrasti* Medic.) (VL), jimsonweed (*Datura stramonium* L.)(JW), tall morning glory (*Ipomea purpurea* L. Roth) (TM), switchgrass (*Panicum virgatum* L.) (SG), barnyard grass (*Echinolchloa crusgalli* (L.) Beauv.) (BG) and green foxtail (*Setaria viridis*) (L.) Beauv.) (GF). The percent control of the weeds compared to untreated checks was determined two weeks after treatment. The results of such testing are summarized in Table III. The data presented in such table indicates the admirable preemergent herbicidal efficacy exhibited by the compounds of this invention.

TABLE III

| Cpd. No. | Preemergence Activity at 11.2 kg/ha Percent Weed Control | | | | | |
|---|---|---|---|---|---|---|
| | VL | JW | TM | BG | SG | GF |
| 1 | 100 | 100 | 100 | 100 | 100 | 100 |
| 2 | 100 | 100 | 100 | 100 | 100 | 100 |
| 3 | 25 | 100 | 90 | 90 | 100 | 100 |
| 4 | 100 | 100 | 100 | 100 | 100 | 100 |
| 5 | 100 | 100 | 100 | 100 | 100 | 100 |
| 6 | 100 | 100 | 100 | 100 | 100 | 100 |
| 7 | 100 | 100 | 100 | 75 | 100 | 100 |
| 8 | 100 | 100 | 100 | 100 | 100 | 100 |
| 9 | 100 | 100 | 90 | 95 | 100 | 100 |
| 10 | 100 | 100 | 100 | 85 | 100 | 100 |
| 11 | 100 | 100 | 100 | 100 | 100 | 100 |
| 12 | 100 | 100 | 80 | 100 | 100 | 85 |
| 13 | 100 | 100 | 100 | 100 | 100 | 100 |
| 14 | 100 | 100 | 100 | 100 | 100 | 100 |
| 15 | 100 | 100 | 100 | 100 | 100 | 100 |
| 16 | 100 | 100 | 95 | 95 | 100 | 100 |
| 17 | 100 | 100 | 100 | 100 | 100 | 100 |
| 18 | 100 | 100 | 100 | 100 | 100 | 100 |
| 19 | 100 | 100 | 95 | 95 | 100 | 100 |
| 20 | 100 | 100 | 100 | 100 | 100 | 100 |

EXAMPLE 5

Postemergence Control

To test the effectiveness of the compounds of this invention as postemergence herbicide, a 3000 ppm solution (produced in accordance with the process described under Example 4) was atomized employing a DeVilbiss [trademark] sprayer, wetting the foliage to the drip point. The remainder of the procedure was the same as described under Example 4. The weeds, which were the same species as described under Example 4, were treated six days after emergence. The percent weed control was evaluated two weeks after treatment. The results of such testing are summarized in Table IV.

TABLE IV

| No. | Postemergence Activity at 3000 ppm Percent Weed Control | | | | | |
|---|---|---|---|---|---|---|
| | VL | JW | TM | BG | SG | GF |
| 1 | 100 | 100 | 100 | 100 | 100 | 100 |
| 2 | 100 | 90 | 100 | 95 | 100 | 100 |
| 3 | 100 | 100 | 100 | 100 | 100 | 100 |
| 4 | 100 | 85 | 100 | 100 | 100 | 100 |
| 5 | 100 | 90 | 100 | 90 | 100 | 100 |
| 6 | 100 | 100 | 100 | 100 | 100 | 100 |
| 7 | 100 | 100 | 100 | 100 | 100 | 100 |
| 8 | 100 | 100 | 100 | 90 | 100 | 100 |
| 9 | 100 | 100 | 100 | 90 | 100 | 100 |
| 10 | 100 | 100 | 100 | 95 | 100 | 100 |
| 11 | 100 | 100 | 100 | 100 | 100 | 100 |
| 12 | 100 | 100 | 95 | 95 | 100 | 100 |
| 13 | 100 | 100 | 100 | 100 | 100 | 100 |
| 14 | 100 | 100 | 100 | 100 | 100 | 100 |

TABLE IV-continued

Postemergence Activity at 3000 ppm
Percent Weed Control

| No. | VL | JW | TM | BG | SG | GF |
|---|---|---|---|---|---|---|
| 15 | 100 | 100 | 100 | 100 | 100 | 100 |
| 16 | 100 | 100 | 100 | 100 | 100 | 100 |
| 17 | 100 | 100 | 100 | 100 | 100 | 100 |
| 18 | 100 | 100 | 100 | 100 | 100 | 100 |
| 19 | 100 | 90 | 100 | 100 | 95 | 100 |
| 20 | 100 | 100 | 100 | 100 | 100 | 100 |

The above results in Table IV demonstrate the excellent postemergent herbicidal activity exhibited by the compounds of this invention.

EXAMPLE 6

Growth Retardation of Beans

Solutions of the compounds of this invention in acetone having a concentration of 1000 ppm were prepared in accordance with the method described in Example 4, above. The foliage of 2 week old bean plants. (*Phaseolus vulgaris* L. cv. Pinto III) was wetted to the drip point with such solution employing a conventional sprayer. As a control, additional bean plants were treated with an acetone/emulsifying agent solutions alone. After 2 weeks in a greenhouse, the plants were evaluated for retardation of vegetative growth. A summary of growth retardation data appears in Table V.

TABLE V

Growth Retardation of Beans (1000 ppm)

| Compound Number | Percent Retardation |
|---|---|
| 1 | 90 |
| 2 | 95 |
| 3 | PT |
| 4 | 100 |
| 5 | 100 |
| 6 | 100 |
| 7 | 100 |
| 8 | 100 |
| 9 | PT |
| 10 | 100 |
| 11 | PT |
| 12 | 20 |
| 13 | PT |
| 14 | 90 |
| 15 | 95 |
| 16 | 90 |
| 17 | 100 |
| 18 | PT |
| 19 | 95 |
| 20 | 100 |

Note:
PT = Phytoxic at this concentration.

The above data indicate the exceptional plant growth regulatory activity exhibited by the compounds of this invention. Although certain of these compounds are phytotoxic to beans at this concentration (and, moreover, several of the compounds were phytotoxic to barley, cotton and/or soybeans at 3000 ppm) it is nevertheless believed that at reduced concentratios and/or employing different means of application these compounds would exhibit plant growth regulatory activity without exhibiting phytotoxic side-effects. (See, e.g., Example 8 with respect to cotton).

EXAMPLE 7

Inhibition of Axillary Branch Growth in Beans

Pinto bean plants were grown in the greenhouse until they had 1 to 3 trifoliolate leaves. The stem was cut off at 2-3 cm above the simple leaves, and any branches in those leaf axils were removed. Spray solutions were prepared and applied in a manner similar to that described in Example 6. After 10-12 days in the greenhouse, any axillary branch growth was removed and weighed, and the percentage of growth control was calculated. The results obtained are summarized in Table VI below.

TABLE VI

| Compound Number | Percent Control (As Percentage of Untreated) | | | |
|---|---|---|---|---|
| | 1000 ppm | 250 ppm | 100 ppm | 10 ppm |
| 5 | 100 | 97 | — | — |
| 6 | 85 | — | 72 | 56 |
| 9 | 98 | — | 47 | — |
| 12 | 100 | — | 34 | — |
| 13 | 97 | — | 0 | — |

"—" indicates not tested

EXAMPLE 8

Cotton Defoliation

Cotton plant (*Gossypium hirsutum* L. "Stoneville 213") having leaves at 3 to 4 nodes were treated with chemical solutions/suspensions (prepared as in Example 6) by immersing the lower leaves. The leaves were removed from the suspension, and the plants placed in the greenhouse. After 2 weeks, the treated leaves were inspected, and the percentage defoliation calculated. The results appear in Table VII below.

TABLE VII

| Compound Number | Percent Defoliation | |
|---|---|---|
| | 1600 ppm | 400 ppm |
| 4 | 63 | 25 |
| 5 | 63 | 0 |
| 6 | 75 | 50 |
| 7 | 88 | 100 |
| 8 | 100 | 75 |
| 10 | 100 | 88 |
| 11 | 100 | 88 |
| 13 | 100 | 100 |
| 14 | 100 | 63 |
| 15 | 100 | 25 |
| 17 | 100 | 63 |
| 18 | 100 | 50 |
| 20 | 100 | 88 |

The above data further indicate the plant growth regulatory effects exhibited by the compounds of this invention.

What is claimed is:

1. A compound of the formula:

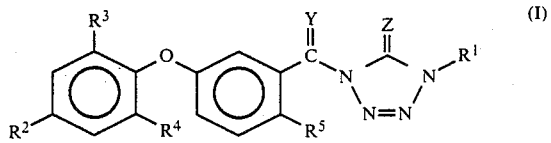

wherein:
Y is oxygen or sulfur;
Z is oxygen or sulfur;
$R^1$ is
$C_1$-$C_{18}$ alkyl,
$C_1$-$C_{12}$ haloalkyl,
$C_2$-$C_{12}$ alkoxyalkyl,
$C_2$-$C_{12}$ alkylthioalkyl,
$C_3$-$C_{10}$ alkenyl, $C_3$–$C_{10}$ cycloalkyl,
$C_5$–$C_{10}$ cycloalkenyl,
$C_7$–$C_{10}$ bridged cycloalkyl or cycloalkenyl,
$C_7$–$C_9$ arylalkyl,
$C_3$–$C_{12}$ alkoxycarbonylalkyl,
$C_5$–$C_6$ aryl,
naphthyl,
pyridyl,
thienyl, or
phenyl substituted with 1–3 substituents each independently selected from the group consisting of halogen, cyano, nitro, $C_1$–$C_4$ haloalkyl, $C_1$–$C_4$ alkyl, $C_2$–$C_4$ dialkylamino, $C_1$–$C_4$ alkoxy, $C_1$–$C_4$ alkylthio, haloalkoxy and phenoxy;

$R^2$ and $R^3$ are each independently halogen, cyano, nitro, $C_1$–$C_4$ alkyl, $C_1$–$C_4$ haloalkyl, $C_1$–$C_4$ alkoxy or $C_1$–$C_4$ haloalkoxy;

$R^4$ is hydrogen, halogen, or trihalomethyl; and $R^5$ is halogen, cyano, nitro, carboxyl, $C_2$–$C_8$ alkoxycarbonyl or of the formula:

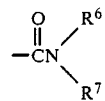

wherein $R^6$ and $R^7$ are each independently hydrogen or $C_1$–$C_4$ alkyl.

2. A compound in accordance with claim 1 wherein:
Y is oxygen;
Z is oxygen;
$R^2$ is chlorine, fluorine or trifluoromethyl;
$R^3$ is chlorine of trifluoromethyl;
$R^4$ is hydrogen;
$R^5$ is nitro;
$R^1$ is phenyl or phenyl having 1–3 substituents, each independently selected from the group consisting of halogen, cyano, nitro haloalkyl, haloalkoxy and 1-naphthyl.

* * * * *